United States Patent
Yamamura et al.

(10) Patent No.: US 12,104,197 B2
(45) Date of Patent: Oct. 1, 2024

(54) PROSTAGLANDIN PRODUCTION METHOD

(71) Applicant: KYOWA PHARMA CHEMICAL CO., LTD., Takaoka (JP)

(72) Inventors: Eitora Yamamura, Takaoka (JP); Jun Ogawa, Kyoto (JP); Akinori Ando, Kyoto (JP)

(73) Assignee: Kyowa Pharma Chemical Co., Ltd., Takaoka (JP)

( * ) Notice: Subject to any disclaimer, the term of this patent is extended or adjusted under 35 U.S.C. 154(b) by 0 days.

(21) Appl. No.: 17/788,289

(22) PCT Filed: Dec. 25, 2020

(86) PCT No.: PCT/JP2020/048629
§ 371 (c)(1),
(2) Date: Jun. 22, 2022

(87) PCT Pub. No.: WO2021/132536
PCT Pub. Date: Jul. 1, 2021

(65) Prior Publication Data
US 2023/0042760 A1    Feb. 9, 2023

(30) Foreign Application Priority Data
Dec. 26, 2019 (JP) .................. 2019-236747

(51) Int. Cl.
*C12P 31/00* (2006.01)

(52) U.S. Cl.
CPC .................... *C12P 31/00* (2013.01)

(58) Field of Classification Search
None
See application file for complete search history.

(56) References Cited

FOREIGN PATENT DOCUMENTS

| | | |
|---|---|---|
| CN | 1182136 A | 5/1998 |
| CN | 105316384 A | 2/2016 |
| JP | S52-054091 A | 5/1977 |
| JP | H06-090788 A | 4/1994 |
| JP | 2007-070335 A | 3/2007 |
| JP | 2012-125229 A | 7/2012 |
| KR | 100796459 B1 | 1/2008 |

OTHER PUBLICATIONS

Dialog, Proquest English translation of JP06090788 A 1994, accessed on May 3, 2023, Japan Patents Fulltext. First available 2013. (Year: 2013).*
Kanamoto et al., "Identification of a Cyclooxygenase Gene from the Red Alga Gracilaria vermiculophylla and Bioconversion of Arachidonic Acid to $PGF_{2\alpha}$ in Engineered *Escherichia coli*," *Appl. Microbiol. Biotechnol.*, 91(4): 1121-1129 (2011).
Japan Patent Office, International Search Report in International Patent Application No. PCT/JP2020/048629 (Feb. 2, 2021).
Japan Patent Office, International Preliminary Report on Patentability in International Patent Application No. PCT/JP2020/048629 (Jul. 7, 2022).
Balaji et al., "Distribution of Cyclooxygenase-1 and Cyclooxygenase-2 in the Mouse Seminal Vesicle," *Journal of Applied Biomedicine*, 6: 97-104 (2008).
Wang, "Prostaglandin E1 Biosynthesized by Dihomo-γ-linolenic Acid and Sheep Seminal Vesicle," *The World's Latest Medical Information Digest*, 16(97): 57 (2016).
European Patent Office, Extended European Search Report in European Patent Application No. 20907000.2 (May 14, 2024).

* cited by examiner

*Primary Examiner* — Robert J Yamasaki
*Assistant Examiner* — Charles Zoltan Constantine
(74) *Attorney, Agent, or Firm* — Leydig, Voit & Mayer, Ltd.

(57) ABSTRACT

A prostaglandin production method according to the present invention comprises reacting an unsaturated fatty acid with cyclooxygenase in the presence of a reducing agent. According to the present invention, it is possible to produce prostaglandins at a high yield.

9 Claims, No Drawings

PROSTAGLANDIN PRODUCTION METHOD

TECHNICAL FIELD

The present invention relates to a prostaglandin production method.

BACKGROUND ART

Conventionally, as a method of producing prostaglandins (PGs), a two-step method in which cyclooxygenase (COX) is reacted (oxidation reaction) with an unsaturated fatty acid to produce $PGG_2$ and/or $PGH_2$, and $PGG_2$ and/or $PGH_2$ is reacted (reduction reaction) with the reducing agent $SnCl_2$ to produce prostaglandin is known (for example, Patent Literature 1 and Non-Patent Literature 2)

CITATION LIST

Patent Literature

[Patent Literature 1] Japanese Unexamined Patent Publication No. H6-90788

Non-Patent Literature

[Non-Patent Literature 1] Applied Microbiol Biotechnol, Vol. 91 (2011) 1121-1129

SUMMARY OF INVENTION

Technical Problem

The yield of prostaglandins obtained by the conventional method was not necessarily high. Therefore, an object of the present invention is to produce a prostaglandin at a high yield.

Solution to Problem

A prostaglandin production method according to the present invention comprises a step of reacting an unsaturated fatty acid with cyclooxygenase in a presence of a reducing agent. The reducing agent may be one or more reducing agents selected from the group consisting of a reducing agent comprising divalent Sn, $Na_2SO_3$, $Na_2S_2O_3$, $Na_2S_2O_4$, and KI, or may be one or more reducing agents selected from the group consisting of a reducing agent comprising divalent Sn and KI, or may be one or more reducing agents selected from the group consisting of $SnCl_2$, $SnSO_4$, $Sn_2P_2O_7$, and $SnC_2O_4$. Alternatively, the reducing agent may be one or more reducing agents selected from the group consisting of $Na_2SO_3$, $Na_2S_2O_3$, and $Na_2S_2O_4$. The unsaturated fatty acid may be an unsaturated fatty acid having 16 or more carbon atoms and having one or more double bonds, and may be one or more unsaturated fatty acids selected from the group consisting of arachidonic acid, dihomo-γ-linolenic acid, and all cis-5,8,11,14,17-eicosapentaenoic acid.

The step of reacting an unsaturated fatty acid with cyclooxygenase in a presence of a reducing agent may be performed at a pH of 6 to 12.5. The step of reacting unsaturated fatty acid with cyclooxygenase in a presence of a reducing agent may comprise adding the unsaturated fatty acid to a mixture of cyclooxygenase and the reducing agent, and the mixture of cyclooxygenase and the reducing agent may be obtained by adding the reducing agent to cyclooxygenase. Cyclooxygenase may be derived from a red alga or mammal. The red alga may be *Gracilaria*, and the mammal may be a human, sheep, or cow. The step of reacting an unsaturated fatty acid with cyclooxygenase in a presence of a reducing agent may comprise bringing the unsaturated fatty acid into contact with cells expressing cyclooxygenase or an extract thereof, or isolated cyclooxygenase in the presence of the reducing agent.

Advantageous Effects of Invention

According to the method of the present invention in which cyclooxygenase is reacted with an unsaturated fatty acid in the presence of a reducing agent, it is possible to produce prostaglandins at a high yield. Conventionally, it is common technical knowledge that, when an oxidation reaction is performed in the presence of a reducing agent, either the oxidation reaction or the reduction reaction does not proceed, and the yield of a desired product decreases. Therefore, it is surprising that prostaglandins can be produced at a high yield by the method of the present invention.

DESCRIPTION OF EMBODIMENTS

A prostaglandin production method according to the present invention comprises a step of reacting an unsaturated fatty acid with cyclooxygenase in the presence of a reducing agent.

The unsaturated fatty acid may be single unsaturated fatty acid or may be a combination of two or more unsaturated fatty acids. The unsaturated fatty acid may be an unsaturated fatty acid having 16 or more or 18 or more carbon atoms and having one or more double bonds. As the unsaturated fatty acid, unsaturated fatty acids that have been conventionally used in the production of prostaglandins such as arachidonic acid (ARA), dihomo-γ-linolenic acid (DGLA), all cis-5,8,11,14,17-eicosapentaenoic acid (EPA), docosapentaenoic acid (DPA), docosahexaenoic acid (DHA), and all-cis-8,11,14,17-eicosatetraenoic acid (ETA) may be used. $PGF_{2\alpha}$ or $PGE_2$ is obtained from ARA, $PGF_{1\alpha}$ or $PGE_1$ is obtained from DGLA, and $PGF_{3\alpha}$ or $PGE_3$ is obtained from EPA. From the viewpoint of accelerating the reaction, a saturated fatty acid may be added together with the unsaturated fatty acid. That is, the step of reacting an unsaturated fatty acid with cyclooxygenase may be performed in the presence of a reducing agent and a saturated fatty acid.

The reducing agent is not particularly limited, and a known reducing agent may be used. The reducing agent may be a single reducing agent or a combination of two or more reducing agents. The reducing agent may be, for example, a reducing agent comprising divalent Sn, $Na_2SO_3$, $Na_2S_2O_3$, $Na_2S_2O_4$, KI, $NaHSO_3$, or $K_2S_2O_3$, or a combination thereof. The reducing agent comprising divalent Sn may be, for example, $SnCl_2$, $SnSO_4$, $Sn_2P_2O_7$, $SnC_2O_4$, or SnO, or a combination thereof. From the viewpoint of selectively obtaining PGF such as $PGF_{2\alpha}$, $PGF_{1\alpha}$, $PGF_{3\alpha}$, at a high yield, the reducing agent is preferably a reducing agent comprising divalent Sn or KI, more preferably a reducing agent comprising divalent Sn, still more preferably $SnCl_2$, $SnSO_4$, $Sn_2P_2O_7$, or $SnC_2O_4$, and particularly preferably $SnCl_2$. From the viewpoint of selectively obtaining PGE such as $PGE_2$, $PGE_1$, and $PGE_3$ at a high yield, the reducing agent is preferably $Na_2SO_3$, $Na_2S_2O_3$, or $Na_2S_2O_4$.

Cyclooxygenase may be a single cyclooxygenase or a combination of two or more cyclooxygenases. The origin of cyclooxygenase (COX) is not particularly limited, and cyclooxygenase may be, for example, cyclooxygenase derived from microorganisms, plants, or animals. The animals may be, for example, mammals. The mammals may be, for example, humans, sheep, or cows. The plants may be, for example, red algae. Red algae may be, for example, *Gracilaria*. The step of reacting an unsaturated fatty acid with cyclooxygenase in the presence of a reducing agent may comprise bringing the unsaturated fatty acid into contact with cells expressing cyclooxygenase or an extract thereof, or isolated cyclooxygenase in the presence of the reducing agent. By bringing the cells expressing cyclooxygenase or the extract thereof into contact with the unsaturated fatty acid, cyclooxygenase in the cells or the extract react with the unsaturated fatty acid. The cells expressing cyclooxygenase may be cells expressing endogenous or exogenous cyclooxygenase. The cells expressing exogenous cyclooxygenase are not particularly limited as long as they are hosts that can express COX, and may be, for example, *E. coli* expressing *Gracilaria*-derived cyclooxygenase (GvCOX). The cells expressing endogenous cyclooxygenase may be, for example, *Gracilaria* cells. Alternatively, the step of reacting an unsaturated fatty acid with cyclooxygenase in the presence of a reducing agent may comprise bringing the unsaturated fatty acid into contact with plants comprising cells expressing cyclooxygenase or an extract thereof, and more specifically, *Gracilaria* or an extract thereof in the presence of the reducing agent.

The initial concentration of the unsaturated fatty acid in a reaction solution comprising the unsaturated fatty acid, reducing agent, and cyclooxygenase may be, for example, 0.0001 to 400 g/L, 0.01 to 100 g/L, or 0.1 to 10 g/L. In this specification, the initial concentration is a concentration immediately after the start of the reaction.

The initial concentration of the reducing agent in the reaction solution comprising the unsaturated fatty acid, reducing agent, and cyclooxygenase may be, for example, 0.0001 to 800 mM, 0.1 to 400 mM, or 1 to 200 mM.

The initial concentration of cyclooxygenase in the reaction solution comprising the unsaturated fatty acid, reducing agent, and cyclooxygenase may be, for example, 0.1 mg/L to 100 g/L, 1 mg/L to 10 g/L, or 10 mg/L to 1 g/L.

In the step of reacting an unsaturated fatty acid with cyclooxygenase in the presence of a reducing agent, the reaction may be performed in water or an aqueous solution. As the aqueous solution, a buffer solution such as an acetic acid buffer solution (pH 4 to 5), a potassium phosphate buffer solution (KPB, pH 6 to 7), a Tris-Cl buffer solution (pH 8 to 10), a boric acid buffer solution (pH 11 to 13), a sodium phosphate buffer solution (NaP, pH 6 to 7), a formic acid buffer solution (pH 3 to 4), or an ammonia buffer solution (pH 9 to 10) may be used. A buffer solution may not necessarily be used as long as the pH can be maintained stably, and the aqueous solution may be, for example, salt water.

The pH of the reaction solution (that is, the pH during the reaction) may be 6 or more, 7 or more, 8 or more, 9 or more, 10 or more, 11 or more, or 12 or more, and may be 12.5 or less, 12 or less, 11 or less, 10 or less, 9 or less, 8 or less, or 7 or less. The pH of the reaction solution is preferably 6 to 12.5, more preferably 7 to 12 or 7 to 12.5, still more preferably 8 to 12 or 8 to 12.5, and particularly preferably 9 to 12.

The temperature of the reaction solution (that is, the temperature of the reaction) is not particularly limited as long as it is a temperature at which cyclooxygenase is not inactivated, and may be, for example, −10 to 90° C., 5 to 70° C., or 20 to 40° C.

The reaction time may be, for example, 30 seconds to 98 hours, 10 minutes to 24 hours, or 30 minutes to 4 hours, although it depends on the reaction speed of the enzyme reaction.

In the step of reacting an unsaturated fatty acid with cyclooxygenase in the presence of a reducing agent, the order in which the unsaturated fatty acid, reducing agent, and cyclooxygenase are added may be, for example, as follows:

The unsaturated fatty acid and the reducing agent may be added to cyclooxygenase, more specifically, a reaction container containing cyclooxygenase, in any order, the unsaturated fatty acid and cyclooxygenase may be added to the reducing agent, more specifically, a reaction container containing the reducing agent, in any order, or cyclooxygenase and the reducing agent may be added to the unsaturated fatty acid, more specifically, a reaction container containing the unsaturated fatty acid, in this order. However, when the reducing agent is added to a mixed solution of the unsaturated fatty acid and cyclooxygenase, it is preferable to add the reducing agent immediately after the unsaturated fatty acid and cyclooxygenase are mixed (for example, within 5 seconds after mixing the unsaturated fatty acid and cyclooxygenase), from the viewpoint of producing prostaglandins at a high yield. In addition, from the viewpoint of selectively obtaining PGF or PGE, it is preferable to add the unsaturated fatty acid to a mixture of cyclooxygenase and the reducing agent, and it is more preferable to add the reducing agent and unsaturated fatty acid in this order to cyclooxygenase, more specifically, a reaction container containing cyclooxygenase. The reaction container is not particularly limited, and conventionally known reaction containers such as microtubes, centrifuge tubes, flasks, beakers, and stainless steel tanks may be used.

In one embodiment, a prostaglandin production method according to the present invention may further comprise, after the step of reacting an unsaturated fatty acid with cyclooxygenase in the presence of a reducing agent, separating cyclooxygenase from the reaction solution, and/or may further comprise extracting a prostaglandin from the reaction solution and purifying the extracted prostaglandin. The method of separating cyclooxygenase is not particularly limited, and known methods may be used. The method of extracting and purifying the prostaglandin is not particularly limited, and known methods may be used. For example, the prostaglandin may be extracted with an organic solvent such as ethyl acetate and then purified by column chromatography.

EXAMPLES

Test Example 1-1

Prostaglandins were produced and analyzed as follows using *E. coli* BL21(DE3)/pGVCOX1.

(1) Preparation of Gene-Expressing Bacterial Cells

GvCOX genes optimized for the codon of *E. coli* were inserted into the NcoI-BamHI site of an *E. coli* expression vector pET-28a (Novagen) to construct plasmid pGVCOX1. The optimized GvCOX genes are described in, for example, Biotechnol. Lett. 36 (2014) 2193-2198. The basic genetic recombination technology in accordance with "Molecular cloning (1989): a laboratory manual. 2nd ed. New York, NY: Cold Spring Laboratory." was followed. Reagents such as restriction enzymes and modifying enzymes used to construct plasmids were purchased from Toyobo Co., Ltd., and used according to the instructions. ECOS (registered trademark) competent *E. coli* BL21(DE3) was purchased from FUJIFILM Wako Pure Chemical Corporation, and pGVCOX1 was introduced into *E. coli* BL21(DE3) in accordance with the instructions to prepare *E. coli* BL21 (DE3)/pGVCOX1.

The *E. coli* BL21(DE3)/pGVCOX1 was inoculated into 5 mL of an LB culture medium (1% triptone, 0.5% yeast extract, 1% sodium chloride) containing 50 mg/L of kanamycin, and cultured with shaking at 28° C. for 24 hours. 2.5 mL of the culture solution was inoculated into 100 mL of an LB culture medium containing 50 mg/L of kanamycin and 0.1 mM isopropyl-β-thiogalactopyranoside (IPTG, Nacalai Tesque, Inc.) and cultured with shaking at 20° C. for 24 hours. 2.5 mL of the culture solution was centrifuged, and the supernatant was removed to obtain GvCOX gene-expressing bacterial cells.

(2) Production of Prostaglandin (Examples)

GvCOX gene-expressing bacterial cells suspended in a buffer solution, a reducing agent suspended in water, and an unsaturated fatty acid were put into a microtube in this order and stirred to obtain 0.5 mL of a mixed solution consisting of the GvCOX gene-expressing bacterial cells, reducing agent, 1 g/L of unsaturated fatty acid, and 50 mM buffer solution. Tris-Cl (pH 8.0) was used as the buffer solution. 5 mM $SnCl_2$, 5 mM $SnSO_4$, 20 mM $Sn_2P_2O_7$, 20 mM $SnC_2O_4$, 5 mM $Na_2SO_3$, 5 mM $Na_2S_2O_3$, 5 mM $Na_2S_2O_4$, or 5 mM KI was used as the reducing agent. Arachidonic acid (Sigma-Aldrich Co. LLC), DGLA (Tokyo Chemical Industry Co., Ltd.) or EPA Tokyo Chemical Industry Co., Ltd.) was used as the unsaturated fatty acid (substrate). The above concentrations are the final concentrations in the mixed solution. The mixed solution was reacted with shaking at 20° C. for 60 minutes. For comparison, the same reaction was performed without adding the reducing agent (reference example). After the reaction was completed, 1 N HCl was added to the reaction solution to adjust the pH to 3.0.

(3) Production of Prostaglandin (Comparative Examples)

GvCOX gene-expressing bacterial cells suspended in a buffer solution and an unsaturated fatty acid were put into a microtube in this order to obtain 0.5 mL of a mixed solution consisting of the GvCOX gene-expressing bacterial cells, 1 g/L unsaturated fatty acid, and 50 mM buffer solution. The mixed solution was reacted with shaking at 20° C. for 60 minutes. After the reaction was completed, 1 N HCl was added to the reaction solution to adjust the pH to 3.0, and a reducing agent was further added. The same buffer solution, reducing agents, and unsaturated fatty acids used in (2) were used as the buffer solution, the reducing agent, and the unsaturated fatty acid.

(4) Analysis of Prostaglandin

A reaction product was extracted from the reaction solution of (2) or (3) using ethyl acetate. The organic solvent was removed from the extract using a rotary evaporator with a diaphragm vacuum pump attached thereto. The obtained precipitate was dissolved in ethanol, and analyzed by LC-MS under the following conditions (reference: Bioscience, Biotechnology, and Biochemistry, Volume 83 (2019) 774-780, D01:10.1080/09168451.2018.1562880).

<LC-MS Analysis Conditions>
Device used: LC-MS2020 (manufactured by Shimadzu Corporation)
Column: 5C18-AR-II COSMOSIL® packed column, 4.6 mm i.d.×150 mm (manufactured by Nacalai Tesque, Inc.)
Column temperature: 40° C.
Eluent A: 0.1% (v/v) formic acid aqueous solution
Eluent B: 0.1% (v/v) formic acid/acetonitrile
Gradient elution (eluent B concentration): 20% to 40% (for 10 minutes), 40% to 100% (for 10 minutes), 100% (for 25 minutes)
Flow rate: 0.2 mL/min
Mode: negative mode
Heat block temperature: 200° C.
Desolvent line temperature: 250° C.
Nebulizer gas flow rate: 1.5 L/min The results are shown in Table 1. In this specification, PGF/PGE indicates a mass ratio of PGF to PGE, and PGE/PGF indicates a mass ratio of PGE to PGF. When ARA, DGLA, and EPA were used as the unsaturated fatty acid, $PGF_{2\alpha}$ and $PGE_2$, $PGF_{1\alpha}$ and $PGE_1$, and $PGF_{3\alpha}$ and $PGE_3$ were obtained, respectively.

TABLE 1

| | Reducing agent | Unsaturated fatty acid | PGF + PGE (mg/L) | PGF/ PGE | PGE/ PGF |
|---|---|---|---|---|---|
| Reference Example | — | ARA | 31.3 | 0.2 | 4.0 |
| Example | $SnCl_2$ | | 190.8 | 24.8 | <0.01 |
| Comparative example | | | 153.6 | 0.3 | 3.4 |
| Example | $Na_2SO_3$ | | 105.0 | 0.2 | 6.4 |
| Comparative example | | | 78.2 | 0.2 | 4.2 |
| Example | $Na_2S_2O_3$ | | 130.4 | 0.3 | 3.5 |
| Comparative example | | | 75.8 | 0.2 | 4.0 |
| Example | $Na_2S_2O_4$ | | 119.9 | 0.1 | 8.4 |
| Comparative example | | | 77.9 | 0.1 | 7.0 |
| Example | KI | | 84.3 | 420.5 | <0.01 |
| Comparative example | | | 52.5 | 0.4 | 2.6 |
| Example | $SnSO_4$ | | 199.5 | 23.0 | <0.01 |
| Comparative example | | | 110.4 | 0.4 | 2.8 |
| Example | $Sn_2P_2O_7$ | | 256.5 | 255.5 | <0.01 |
| Comparative example | | | 144.8 | 0.1 | 19.7 |
| Example | $SnC_2O_4$ | | 165.9 | 82.0 | <0.01 |
| Comparative example | | | 63.4 | 0.1 | 11.2 |
| Reference example | — | DGLA | 12.5 | 0.2 | 5.6 |
| Example | $SnCl_2$ | | 50.4 | 37.8 | <0.01 |
| Comparative example | | | 42.5 | 0.2 | 5.4 |
| Example | $Na_2SO_3$ | | 33.9 | 0.2 | 4.2 |
| Comparative example | | | 28.6 | 0.1 | 8.2 |
| Example | $Na_2S_2O_3$ | | 41.8 | 0.3 | 3.4 |
| Comparative example | | | 38.4 | 0.2 | 5.1 |
| Example | $Na_2S_2O_4$ | | 37.3 | 0.4 | 2.3 |
| Comparative example | | | 26.5 | 0.1 | 10.0 |

TABLE 1-continued

| | Reducing agent | Unsaturated fatty acid | PGF + PGE (mg/L) | PGF/PGE | PGE/PGF |
|---|---|---|---|---|---|
| Reference example | — | EPA | 6.0 | 0.1 | 12.7 |
| Example | SnCl$_2$ | | 32.5 | 91.7 | <0.01 |
| Comparative example | | | 29.0 | 0.3 | 3.8 |
| Example | | | 13.1 | <0.01 | 64.5 |
| Comparative example | Na$_2$SO$_3$ | | 12.0 | 0.1 | 9.9 |
| Example | | | 19.1 | 0.1 | 10.9 |
| Comparative example | Na$_2$S$_2$O$_3$ | | 17.9 | 0.1 | 10.2 |
| Example | | | 14.4 | <0.01 | 27.8 |
| Comparative example | Na$_2$S$_2$O$_4$ | | 11.0 | 0.1 | 6.9 |

(5) Control Experiment pET-28a was introduced into *E. coli* BL21(DE3) to obtain *E. coli* BL21(DE3)/pET-28a. When the experiments (2) to (4) were conducted using *E. coli* BL21(DE3)/pET-28a in place of GvCOX gene-expressing bacterial cells, no prostaglandin was detected.

Test Example 1-2

Prostaglandins were produced and analyzed as follows using the extract of *E. coli* BL21(DE3)/pGVCOX1.

(1) Preparation of GvCOX Extract

The *E. coli* BL21(DE3)/pGVCOX1 prepared by the method described in Test Example 1-1 was inoculated into 5 mL of an LB culture medium containing 50 mg/L of kanamycin, and cultured with shaking at 28° C. for 24 hours. 2.5 mL of the culture solution was inoculated into 100 mL of an LB culture medium containing 50 mg/L of kanamycin and 0.1 mM IPTG and cultured with shaking at 20° C. for 24 hours. The culture solution was centrifuged, and the supernatant was removed. The obtained bacterial cells were suspended in 10 mL of 50 mM Tris-Cl (pH 8.0), and crushed using Ultrasonic Homogenizer US-300 (manufactured by Nissei Corporation) to obtain an extract of the GvCOX gene-expressing bacterial cells (GvCOX extract).

(2) Production and Analysis of Prostaglandin (Examples and Comparative Examples)

Prostaglandins were produced and analyzed in the same manner as in (2) to (4) of Test Example 1-1 except that 0.25 mL of the GvCOX extract was used in place of the GvCOX gene-expressing bacterial cells. The same buffer solution as in Test Example 1-1 was used as the buffer solution. SnCl$_2$, SnSO$_4$, or Na$_2$SO$_3$ at a final concentration of 5 mM was used as the reducing agent. Arachidonic acid was used as the unsaturated fatty acid. The results are shown in Table 2.

TABLE 2

| | Reducing agent | Unsaturated fatty acid | PGF$_{2\alpha}$ + PGE$_2$ (mg/L) | PGF$_{2\alpha}$/PGE$_2$ | PGE$_2$/PGF$_{2\alpha}$ |
|---|---|---|---|---|---|
| Reference example | — | ARA | 38.4 | 0.1 | 8.4 |
| Example | SnCl$_2$ | | 212.4 | 176.0 | <0.01 |
| Comparative example | | | 84.5 | 0.1 | 14.1 |
| Example | SnSO$_4$ | | 197.2 | 218.1 | <0.01 |
| Comparative example | | | 96.5 | 0.1 | 10.5 |
| Example | Na$_2$SO$_3$ | | 102.4 | 0.1 | 15.5 |
| Comparative example | | | 63.2 | 0.2 | 6.2 |

(3) Control Experiment

When the experiment of (2) was performed using *E. coli* BL21(DE3)/pET-28a in place of the GvCOX extract, no prostaglandin was detected.

Test Example 1-3

Prostaglandins were produced and analyzed as follows using sheep-derived COX-1.

(1) Production of Prostaglandin (Examples)

Sheep-derived COX-1 (Funakoshi Co., Ltd.), a reducing agent suspended in water, and an unsaturated fatty acid were put into a microtube in this order and stirred to obtain 0.5 mL of a mixed solution consisting of 5 μg of sheep-derived COX-1, the reducing agent, the unsaturated fatty acid, and 50 mM buffer solution. Tris-Cl (pH 8.0) was used as the buffer solution. 0.1 mM SnCl$_2$, 5 mM Na$_2$SO$_3$, 5 mM Na$_2$S$_2$O$_3$, or 5 mM Na$_2$S$_2$O$_4$ was used as the reducing agent. 0.1 g/L of ARA, 0.1 g/L of DGLA, or 0.1 g/L of EPA was used as the unsaturated fatty acid. The above concentrations are the final concentrations in the mixed solution. The mixed solution was reacted at 37° C. for 60 minutes. For comparison, the same reaction was performed without adding the reducing agent (reference example). After the reaction was completed, 1 N HCl was added to the reaction solution to adjust the pH to 3.0.

(2) Production of Prostaglandin (Comparative Examples)

Sheep-derived COX-1 (Funakoshi Co., Ltd.) and an unsaturated fatty acid were put into a microtube in this order and stirred to obtain 0.5 mL of a mixed solution consisting of 5 μg of sheep-derived COX-1, the unsaturated fatty acid, and 50 mM buffer solution. The mixed solution was reacted at 37° C. for 60 minutes. After the reaction was completed, 1 N HCl was added to the reaction solution to adjust the pH to 3.0, and a reducing agent was further added. The same buffer solution, reducing agent, and unsaturated fatty acids used in (1) were used as the buffer solution, the reducing agent, and the unsaturated fatty acid.

(3) Analysis of Prostaglandin

Prostaglandins in the reaction solutions of (1) and (2) were analyzed in the same manner as in (4) of Test Example 1-1. The results are shown in Table 3.

TABLE 3

| Unsaturated fatty acid | Reducing agent | PGF + PGE (µg/L) | PGF/PGE | PGE/PGF |
|---|---|---|---|---|
| Reference example | ARA | — | 11.9 | 0.5 | 1.9 |
| Example | | SnCl$_2$ | 87.3 | 872.0 | <0.01 |
| Comparative example | | SnCl$_2$ | 53.2 | 0.1 | 12.0 |
| Example | | Na$_2$SO$_3$ | 74.9 | <0.01 | 748.0 |
| Comparative example | | Na$_2$SO$_3$ | 20.9 | <0.01 | 208.0 |
| Example | | Na$_2$S$_2$O$_3$ | 59.7 | 0.2 | 4.6 |
| Comparative example | | Na$_2$S$_2$O$_3$ | 27.7 | 0.7 | 3.2 |
| Example | | Na$_2$S$_2$O$_4$ | 30.7 | <0.01 | 306.0 |
| Comparative example | | Na$_2$S$_2$O$_4$ | 15.8 | 0.5 | 1.9 |
| Reference example | DGLA | — | 4.5 | 0.1 | 10.3 |
| Example | | SnCl$_2$ | 24.2 | 17.6 | 0.1 |
| Comparative example | | SnCl$_2$ | 19.7 | 0.1 | 11.3 |
| Example | | Na$_2$SO$_3$ | 18.2 | 0.1 | 9.1 |
| Comparative example | | Na$_2$SO$_3$ | 13.2 | 0.1 | 13.7 |
| Example | | Na$_2$S$_2$O$_3$ | 15.3 | 0.1 | 11.8 |
| Comparative example | | Na$_2$S$_2$O$_3$ | 10.1 | 0.1 | 11.6 |
| Example | | Na$_2$S$_2$O$_4$ | 9.5 | 0.1 | 14.8 |
| Comparative example | | Na$_2$S$_2$O$_4$ | 6.9 | 0.1 | 8.9 |
| Reference example | EPA | — | 0.9 | 0.1 | 8.0 |
| Example | | SnCl$_2$ | 4.4 | 21.0 | <0.01 |
| Comparative example | | SnCl$_2$ | 1.7 | 0.4 | 2.4 |
| Example | | Na$_2$SO$_3$ | 2.5 | <0.01 | 24.0 |
| Comparative example | | Na$_2$SO$_3$ | 1.8 | 0.1 | 8.0 |
| Example | | Na$_2$S$_2$O$_3$ | 2.0 | 0.1 | 19.0 |
| Comparative example | | Na$_2$S$_2$O$_3$ | 1.5 | 0.2 | 6.5 |
| Example | | Na$_2$S$_2$O$_4$ | 1.8 | 0.1 | 17.0 |
| Comparative example | | Na$_2$S$_2$O$_4$ | 1.2 | 0.1 | 11.0 |

(4) Control Experiment

When the experiments of (1) to (3) were performed without using COX-1, no prostaglandin was detected.

Test Example 1-4

Prostaglandins were produced and analyzed using human-derived COX-1 as follows.

(1) Production and Analysis of Prostaglandin (Examples and Comparative Examples)

Prostaglandins were produced and analyzed in the same manner as in Test Example 1-3 except that Human PTGS1/COX-1 (Funakoshi Co., Ltd.) was used in place of sheep-derived COX-1, and the type of the reducing agent was changed. Specifically, Tris-Cl (pH 8.0) was used as the buffer solution, 0.1 mM SnCl$_2$ or 0.1 mM SnSO$_4$ was used as the reducing agent, and arachidonic acid was used as the unsaturated fatty acid. The results are shown in Table 4.

TABLE 4

| Unsaturated fatty acid | Reducing agent | PGF$_{2\alpha}$ + PGE$_2$ (µg/L) | PGF$_{2\alpha}$/PGE$_2$ | PGE$_2$/PGF$_{2\alpha}$ |
|---|---|---|---|---|
| Reference example | ARA | — | 12.7 | 0.1 | 10.5 |
| Example | | SnCl$_2$ | 98.1 | 27.0 | <0.01 |
| Comparative example | | SnCl$_2$ | 63.9 | 0.6 | 1.6 |
| Example | | SnSO$_4$ | 93.2 | 83.7 | <0.01 |
| Comparative example | | SnSO$_4$ | 52.3 | 0.6 | 1.7 |

(2) Control Experiment

When the experiment of (1) was performed without using Human PTGS1/COX-1, no prostaglandin was detected.

Test Example 1—Results

In examples in which cyclooxygenase was reacted with an unsaturated fatty acid in the presence of a reducing agent, it was possible to obtain prostaglandins at a high yield. In addition, when a reducing agent comprising divalent Sn or KI was used as the reducing agent, PGF (PGF$_{2\alpha}$, PGF$_{1\alpha}$, or PGF$_{3\alpha}$) was selectively obtained. On the other hand, when Na$_2$SO$_3$, Na$_2$S$_2$O$_3$, or Na$_2$S$_2$O$_4$ was used as the reducing agent, PGE (PGE$_2$, PGE$_1$, or PGE$_3$) was selectively obtained.

Test Example 2

Prostaglandins were produced and analyzed in the same manner as in (2) and (4) of Test Example 1-1 except that an acetic acid buffer solution (pH 4.0 or 5.0) at a final concentration of 100 mM, KPB (pH 6.0 or 7.0), a Tris-Cl buffer solution (pH 8.0, 9.0, or 10.0), or a boric acid buffer solution (pH 11.0, 12.0, 12.5, or 13.0) was used as the buffer solution, and the final concentration of the reducing agent was changed. Specifically, 5 mM SnCl$_2$, 5 mM SnSO$_4$, 25 mM Sn$_2$P$_2$SO$_7$, or 25 mM SnC$_2$O$_4$ was used as the reducing agent, and arachidonic acid was used as the unsaturated fatty acid. The above concentrations are the final concentrations in the mixed solution. The results are shown in Table 5.

TABLE 5

| Reducing agent | pH | PGF$_{2\alpha}$ + PGE$_2$ (mg/L) | PGF$_{2\alpha}$/PGE$_2$ | PGE$_2$/PGF$_{2\alpha}$ |
|---|---|---|---|---|
| SnCl$_2$ | 4.0 | <0.01 | — | — |
| | 5.0 | <0.01 | — | — |
| | 6.0 | 5.9 | 6.4 | 0.2 |
| | 7.0 | 69.8 | 13.9 | 0.1 |
| | 8.0 | 198.6 | 15.6 | 0.1 |
| | 9.0 | 239.9 | 10.8 | 0.1 |
| | 10.0 | 268.1 | 11.5 | 0.1 |
| | 11.0 | 313.8 | 11.1 | 0.1 |
| | 12.0 | 359.0 | 9.4 | 0.1 |
| | 12.5 | 14.0 | 4.8 | 0.2 |
| | 13.0 | <0.01 | — | — |
| SnSO$_4$ | 4.0 | <0.01 | — | — |
| | 5.0 | <0.01 | — | — |
| | 6.0 | 23.7 | 2.7 | 0.4 |
| | 7.0 | 87.8 | 5.0 | 0.2 |
| | 8.0 | 214.5 | 11.2 | 0.1 |
| | 9.0 | 260.2 | 11.6 | 0.1 |
| | 10.0 | 279.2 | 11.0 | 0.1 |

TABLE 5-continued

| Reducing agent | pH | $PGF_{2\alpha}$ + $PGE_2$ (mg/L) | $PGF_{2\alpha}/PGE_2$ | $PGE_2/PGF_{2\alpha}$ |
|---|---|---|---|---|
|  | 11.0 | 298.5 | 11.0 | 0.1 |
|  | 12.0 | 317.2 | 12.8 | 0.1 |
|  | 12.5 | 22.5 | 3.6 | 0.3 |
|  | 13.0 | <0.01 | — | — |
| $Sn_2P_2O_7$ | 4.0 | <0.01 | — | — |
|  | 5.0 | <0.01 | — | — |
|  | 6.0 | 22.9 | 44.8 | <0.01 |
|  | 7.0 | 52.3 | 36.4 | <0.01 |
|  | 8.0 | 173.0 | 95.1 | <0.01 |
|  | 9.0 | 255.3 | 110.0 | <0.01 |
|  | 10.0 | 305.3 | 116.4 | <0.01 |
|  | 11.0 | 346.9 | 92.8 | <0.01 |
|  | 12.0 | 384.8 | 47.7 | <0.01 |
|  | 12.5 | 162.2 | 22.5 | <0.01 |
|  | 13.0 | <0.01 | — | — |
| $SnC_2O_4$ | 4.0 | <0.01 | — | — |
|  | 5.0 | <0.01 | — | — |
|  | 6.0 | 0.9 | 8.0 | 0.1 |
|  | 7.0 | 15.8 | 9.5 | 0.1 |
|  | 8.0 | 122.2 | 66.9 | <0.01 |
|  | 9.0 | 173.0 | 14.7 | 0.1 |
|  | 10.0 | 207.8 | 16.2 | 0.1 |
|  | 11.0 | 219.1 | 10.7 | 0.1 |
|  | 12.0 | 251.8 | 9.5 | 0.1 |
|  | 12.5 | 124.1 | 4.6 | 0.2 |
|  | 13.0 | <0.01 | — | — |

Test Example 2—Results

By performing the reaction in a specific pH range, it was possible to obtain prostaglandins at a higher yield.

[Test Example 3-1] (Examples)

Prostaglandins were produced and analyzed in the same manner as in (2) and (4) of Test Example 1-1 except that the final concentrations of the buffer solution and the reducing agent were changed. Specifically, 100 mM Tris-Cl (pH 8.0) was used as the buffer solution, 10 mM $SnCl_2$, 10 mM $SnSO_4$, 25 mM $Sn_2P_2O_7$, or 25 mM $SnC_2O_4$ was used as the reducing agent, and 1 g/L of arachidonic acid was used as the unsaturated fatty acid. The above concentrations are the final concentrations in the mixed solution.

[Test Example 3-2] (Examples)

Prostaglandins were produced and analyzed in the same manner as in Test Example 3-1 except that the composition of the mixed solution and the preparation method thereof were changed as follows: a buffer solution, a reducing agent suspended in water, arachidonic acid, and GvCOX gene-expressing bacterial cells suspended in a buffer solution were put into a microtube in this order and stirred to obtain 0.5 mL of a mixed solution consisting of the GvCOX gene-expressing bacterial cells, 25 mM reducing agent, 2.5 g/L of arachidonic acid, and 100 mM Tris-Cl (pH 8.0).

[Test Example 3-3] (Comparative Examples)

Prostaglandins were produced and analyzed in the same manner as in (3) and (4) of Test Example 1-1 except that the final concentrations of the buffer solution and the reducing agent were changed. Specifically, 100 mM Tris-Cl (pH 8.0) was used as the buffer solution, 10 mM $SnCl_2$, 10 mM $SnSO_4$, 25 mM $Sn_2P_2O_7$, or 25 mM $SnC_2O_4$ was used as the reducing agent, and 1 g/L of arachidonic acid was used as the unsaturated fatty acid. The above concentrations are the final concentrations in the mixed solution.

Test Example 3—Results

The results of Test Examples 3-1 to 3-3 are shown in Table 6.

TABLE 6

|  | Reducing agent | Order of addition | $PGF_{2\alpha}$ + $PGE_2$ (mg/L) | $PGF_{2\alpha}/PGE_2$ | $PGE_2/PGF_{2\alpha}$ |
|---|---|---|---|---|---|
| Example | $SnCl_2$ | (1)COX (2)Reducing Agent (3)Substrate | 186.8 | 24.9 | <0.01 |
|  |  | (1)Reducing Agent (2)Substrate (3)COX | 225.7 | 21.6 | <0.01 |
| Comparative example |  | Reducing agent added after COX reaction | 135.5 | 0.1 | 7.7 |
| Example | $SnSO_4$ | (1)COX (2)Reducing Agent (3)Substrate | 206.7 | 19.7 | 0.1 |
|  |  | (1)Reducing Agent (2)Substrate (3)COX | 211.0 | 7.7 | 0.1 |
| Comparative example |  | Reducing agent added after COX reaction | 95.8 | 0.1 | 15.2 |
| Example | $Sn_2P_2O_7$ | (1)COX (2)Reducing Agent (3)Substrate | 256.5 | 255.5 | <0.01 |
|  |  | (1)Reducing Agent (2)Substrate (3)COX | 253.4 | 32.3 | <0.01 |
| Comparative example |  | Reducing agent added after COX reaction | 144.8 | 0.1 | 19.7 |
| Example | $SnC_2O_4$ | (1)COX (2)Reducing Agent (3)Substrate | 165.9 | 82.0 | <0.01 |
|  |  | (1)Reducing Agent (2)Substrate (3)COX | 149.4 | 13.1 | 0.1 |
| Comparative example |  | Reducing agent added after COX reaction | 90.4 | 0.1 | 16.4 |

When the GvCOX gene-expressing bacterial cells, the reducing agent, and arachidonic acid were added in this order, $PGF_{2\alpha}$ was obtained more selectively than when the reducing agent, arachidonic acid, and the GvCOX gene-expressing bacterial cells were added in this order.

The invention claimed is:

1. A prostaglandin production method, comprising a step of reacting an unsaturated fatty acid with cyclooxygenase in a presence of a reducing agent at a pH of 8 to 12, wherein the reducing agent is one or more reducing agents selected from the group consisting of a divalent Sn reducing agent and KI, wherein the step of reacting an unsaturated fatty acid with cyclooxygenase in a presence of a reducing agent at a pH of 8 to 12 comprises:

(i) adding the reducing agent and then the unsaturated fatty acid in sequential order to the cyclooxygenase or (ii) adding the unsaturated fatty acid and then the cyclooxygenase in sequential order to the reducing agent; and, wherein the method selectively produces prostaglandin Fs over prostaglandin Gs.

2. The method according to claim 1, wherein the reducing agent is one or more reducing agents selected from the group consisting of $SnCl_2$, $SnSO_4$, $Sn_2P_2O_7$, and $SnC_2O_4$.

3. The method according to claim 1, wherein the unsaturated fatty acid is an unsaturated fatty acid having 16 or more carbon atoms and having one or more double bonds.

4. The method according to claim 3, wherein the unsaturated fatty acid having 16 or more carbon atoms and having one or more double bonds is one or more unsaturated fatty acids selected from the group consisting of arachidonic acid, dihomo-γ-linolenic acid, and all cis-5,8,11,14,17-eicosapentaenoic acid.

5. The method according to claim 1, wherein the step of reacting an unsaturated fatty acid with cyclooxygenase in a presence of a reducing agent at a pH of 8 to 12 comprises (i) adding the reducing agent and then the unsaturated fatty acid in sequential order to the cyclooxygenase.

6. The method according to claim 1, wherein the cyclooxygenase is derived from a red alga or mammal.

7. The method according to claim 6, wherein the red alga is *Gracilaria*, and the mammal is a human, sheep, or cow.

8. The method according to claim 1, wherein the step of reacting an unsaturated fatty acid with cyclooxygenase in a presence of a reducing agent at a pH of 8 to 12 comprises bringing the unsaturated fatty acid into contact with cells expressing cyclooxygenase, an extract thereof, or an isolated cyclooxygenase.

9. The method according to claim 1, wherein the step of reacting an unsaturated fatty acid with cyclooxygenase in a presence of a reducing agent at a pH of 8 to 12 comprises (ii) adding the unsaturated fatty acid and then the cyclooxygenase in sequential order to the reducing agent.

* * * * *